(12) United States Patent
Babchenko

(10) Patent No.: US 8,761,865 B2
(45) Date of Patent: Jun. 24, 2014

(54) OPTICAL SENSOR AND A METHOD OF ITS USE

(76) Inventor: Anatoly Babchenko, Jerusalem (IL)

( * ) Notice: Subject to any disclaimer, the term of this patent is extended or adjusted under 35 U.S.C. 154(b) by 1876 days.

(21) Appl. No.: 11/886,052

(22) PCT Filed: Mar. 8, 2006

(86) PCT No.: PCT/IL2006/000305
§ 371 (c)(1),
(2), (4) Date: May 7, 2008

(87) PCT Pub. No.: WO2006/095343
PCT Pub. Date: Sep. 14, 2006

(65) Prior Publication Data
US 2008/0221456 A1 Sep. 11, 2008

(30) Foreign Application Priority Data

Mar. 10, 2005 (IL) .......................................... 167361
Feb. 23, 2006 (IL) .......................................... 173894

(51) Int. Cl.
*A61B 6/00* (2006.01)
*A61B 5/00* (2006.01)
*A61B 5/022* (2006.01)

(52) U.S. Cl.
CPC ............ *A61B 5/0075* (2013.01); *A61B 5/0084* (2013.01); *A61B 5/0086* (2013.01); *A61B 5/022* (2013.01); *A61B 5/6848* (2013.01)
USPC ........... 600/473; 600/476; 600/478; 600/485; 600/490; 600/494; 600/567

(58) Field of Classification Search
CPC .. A61B 5/0075; A61B 5/0084; A61B 5/0086; A61B 5/022; A61B 5/6848
USPC .................................. 600/407, 102, 342, 476
See application file for complete search history.

(56) References Cited

U.S. PATENT DOCUMENTS 4,556,438 A 12/1985 Hoffmeister et al.
5,349,954 A 9/1994 Tiemann et al.
(Continued)

FOREIGN PATENT DOCUMENTS

| WO | WO90/01697 A1 | 2/1990 |
| WO | 99/07277 A | 2/1999 |
| WO | 2004/016163 A | 2/2004 |

OTHER PUBLICATIONS

International Preliminary Report on Patentability for PCT/IL2006/000305, mailed on Jun. 27, 2006, 3 pages.
(Continued)

*Primary Examiner* — Baisakhi Roy
(74) *Attorney, Agent, or Firm* — Kilpatrick Townsend & Stockton LLP

(57) ABSTRACT

The invention provides a device 10 for analysis of tissue cells 12 in a living body, the device comprising a stylet 14, the stylet comprising a clad optical fiber senior 18 enveloped in a tubular jacket 20, wherein an unclad area 24 of the fiber and a jacket window 26 corresponding to the unclad area are proximate to the distal end 28 thereof, the optical fiber 18 being linked at a proximate end 30 to receive light from a light source 32, the device further including a light analyzer 34 for measuring qualities of output light at the depth at which the unclad area 24 is positioned in the body during use, an electronic data processor 36 being linked between the light analyzer 34 and a display 38 provided to show real-time data regarding any area 40 evidencing a change in optical properties of body tissues being successively examined.

21 Claims, 3 Drawing Sheets

(56) References Cited

U.S. PATENT DOCUMENTS

| | | | |
|---|---|---|---|
| 5,452,723 A * | 9/1995 | Wu et al. | 600/342 |
| 5,607,389 A | 3/1997 | Edwards et al. | |
| 5,807,261 A * | 9/1998 | Benaron et al. | 600/473 |
| 5,938,595 A | 8/1999 | Glass et al. | |
| 5,954,655 A * | 9/1999 | Hussman | 600/478 |
| 6,269,066 B1 * | 7/2001 | Chase | 369/126 |
| 6,366,726 B1 | 4/2002 | Wach et al. | |
| 6,500,114 B1 | 12/2002 | Petitto et al. | |
| 6,564,087 B1 | 5/2003 | Pitris et al. | |
| 6,647,285 B2 | 11/2003 | Da Silva et al. | |
| 6,749,576 B2 | 6/2004 | Bauer | |
| 7,761,139 B2 * | 7/2010 | Tearney et al. | 600/473 |
| 7,903,254 B2 * | 3/2011 | Wax et al. | 356/456 |
| 8,066,681 B1 * | 11/2011 | Hall et al. | 604/264 |
| 2004/0075826 A1 * | 4/2004 | Ro et al. | 356/73.1 |
| 2006/0195014 A1 * | 8/2006 | Seibel et al. | 600/102 |
| 2007/0014692 A1 * | 1/2007 | Erb et al. | 422/82.11 |
| 2008/0004842 A1 * | 1/2008 | Amelink et al. | 702/190 |

OTHER PUBLICATIONS

International Search Report for PCT/IL2006/000305, mailed on Sep. 12, 2007, 8 pages.

Weiss et al., "Video-intuboscopic assistance is a useful aid to tracheal intubation in pediatric patients", Cardiothoracic Anaesthesia, Respiration and Airway, 2001, vol. 48, No. 7, p. 691-696.

Weiss et al., "Appropriate placement of intubation depth marks in a new cuffed paediatric tracheal tube", British Journal of Anaestheaia, 2005, vol. 94, No. 1, p. 80-87.

Weiss et al., "Shortcomings of cuffed paediatric tracheal tubes", British Journal of Anaesthesia, 2004, vol. 92, No. 1, p. 78-88.

Weiss, M., "Video-intuboscopy: A new aid to routine and difficult tracheal intubation", British Journal of Anaesthesia, 1998, vol. 80, No. 4, p. 525-527.

* cited by examiner

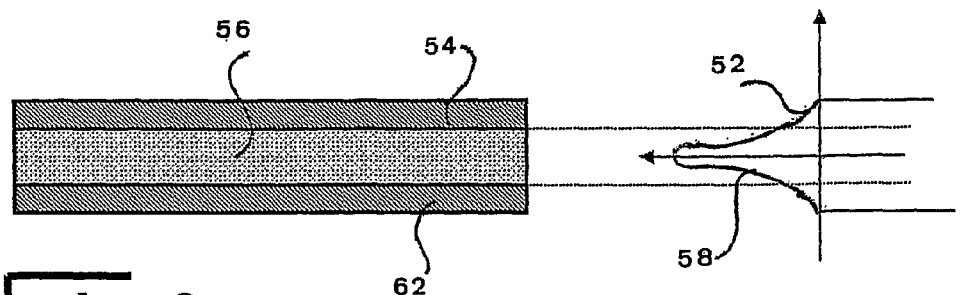
Fig. 3
Fig. 4
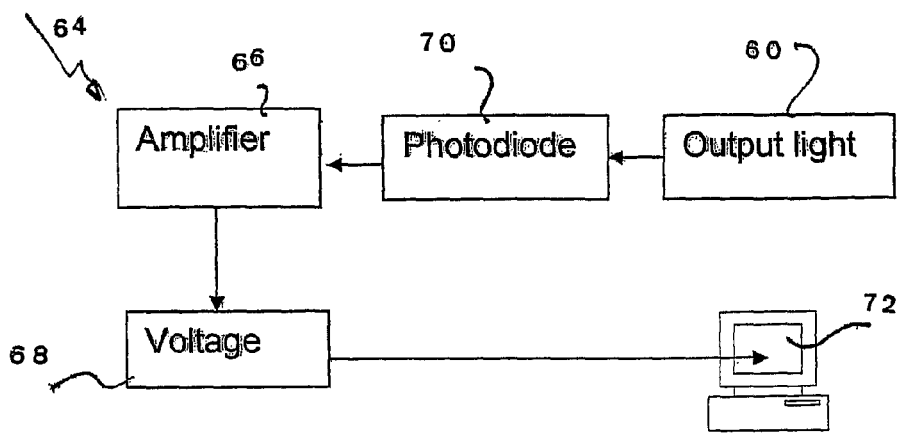
Fig. 5
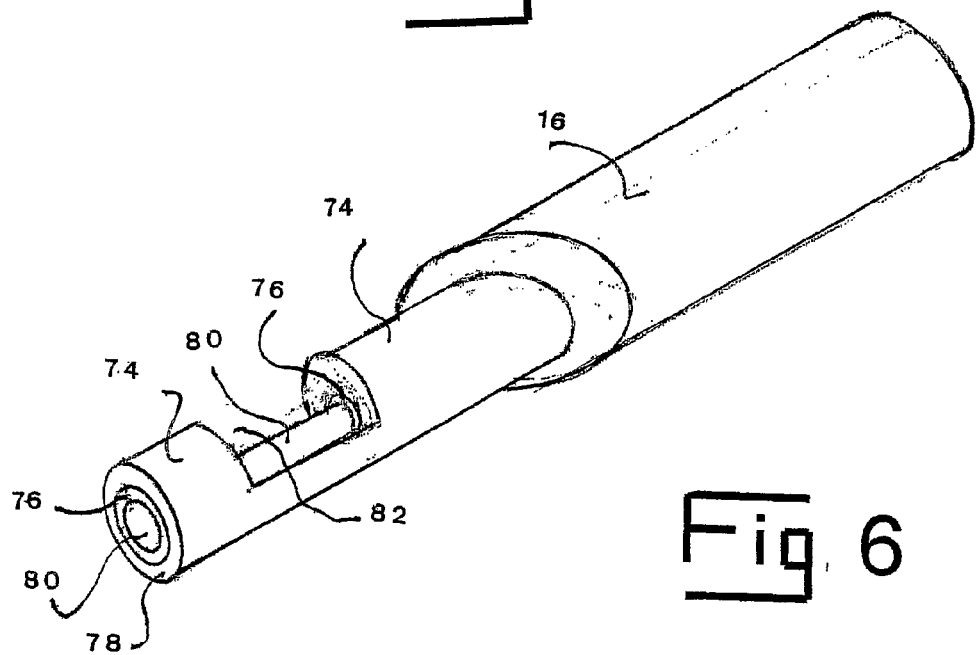
Fig. 6

OPTICAL SENSOR AND A METHOD OF ITS USE

The present invention relates to the field of medical tissue analysis and biopsies.

More particularly, there is provided a real-time optical instrument using an innovative stylet to act as a sensor for analyzing and identifying characterizing features of body tissue in which it is inserted as well as for the detection and diagnosis of suspected cancer and other tissue pathologies and for instrument positioning and tissue interrogation in the body. Methods for the use of said instrument are also provided.

Final diagnosis of a malignant tumor relies on the removal and histological determination of a small specimen of body tissue from the suspected area. The biopsy procedure requires the accurate incursion of a biopsy needle through the surrounding healthy tissue and into a suspected malignancy or other abnormal tissue. The needle can then be used to remove a biopsy sample. This procedure must be accurate since the final diagnosis will rely on the histological analysis of the sample removed by the biopsy tool.

Today, the degree of success of a biopsy depends on the physician's ability to accurately hit the target cells using imaging techniques such as ultrasound (US) or computerized tomography (CT) as a guide. Furthermore, at times up to a dozen tissue samples are taken to ensure that the biopsy will not miss its target. Despite these efforts, there is still a rate of 7% missed diagnosis in addition to 6% of the biopsies, which are inconclusive.

Recent developments and improvements to the biopsy procedures are seen in the following U.S. Patents.

In U.S. Pat. No. 4,566,438 Liese et al, disclose a stylet having a beveled end. The hollow stylet contains two optical fibers, one for incoming and one for outgoing light. The apparatus is claimed to be capable of determining the area in which the needle is positioned within the body.

Edwards et al. in U.S. Pat. No. 5,607,389 propose a medical probe apparatus comprising a catheter having a stylet guide for directing a flexible stylet outward through a stylet port and through intervening tissue to target tissues. Several alternative mechanisms are described allowing the stylet tip to capture cell samples.

In U.S. Pat. No. 5,938,595 Glass et al., disclose an optical system, which includes a fiber optic sensor for D dimer. The system is intended for the diagnosis of stroke-related conditions in humans.

Wach et all describe a large variety of distal ends for the fiber optic probes in U.S. Pat. No. 6,366,726, the aim being to use the distal extremity of the central fiber to illuminate the biological medium being investigated and to collect light by means of further fibers surrounding said central fiber.

A method of extracting biopsy cells from a breast is disclosed by Petitto et al. in U.S. Pat. No. 6,500,114 B1. The instrument described can be coupled to a display screen for depth-of-field viewing.

Pitris et al disclose a fiber optic needle probe in U.S. Pat. No. 6,564,087 for imaging, particularly for optical coherence tomography imaging. Light is supplied and received through a side window of the probe. To scan a biological specimen motion of the needle or optic fiber or beam director is produced by an actuator.

In U.S. Pat. No. 6,647,285 B2 Da Silva et al., describe a further optical probe. They claim a novel feature—prevention of light fluctuations.

A further novelty, a biopsy device enabling the physician to adjust the size of the sample to be removed, is claimed by Bauer in U.S. Pat. No. 6,749,576 B2.

A pediatric video-optical intubation stylet is described by Weiss in the Internet Journal of Anesthesiology (ISSN 1092). An interesting feature thereof is an arrangement for a flow of oxygen at the stylet tip. The gas flow is directed at the distal lens to prevent fogging and blockage by secretions.

From the above it can be seen that in prior art devices the light reflected or received into the stylet is used for informing the physician where the probe is currently positioned or provides the data, which is collected to build up a picture of the examined area.

It is now one of the objects of the present invention to obviate the disadvantages of prior art stylet probes, and to provide a fiber optic instrument, which is able to sense in real time the optical properties of body tissue in contact with the fiber optic stylet.

It is a further object of the present invention to provide methods for the use of said instrument.

According to the present invention there is now provided a device for analysis of tissue cells in a living body, said device comprising a stylet, said stylet comprising a clad optical fiber sensor enveloped in a tubular jacket, wherein an unclad area of said fiber and a jacket window corresponding to said unclad area are proximate to the distal end thereof, said optical fiber being linked at a proximate end to receive light from a light source, the device further including a light analyzer for measuring qualities of output light at the depth at which said unclad area is positioned in said body during use, an electronic data processor being linked between said light analyzer and a display provided to show real-time data regarding any area evidencing a change in optical properties of body tissues being successively examined.

The term body tissues as used herein includes blood and other bodily fluids and is not intended to exclude any substance or material that may be found inside or on the surface of a living body.

In preferred embodiments of the present invention, said device is used for biopsy testing.

In another preferred embodiment of the present invention said device can be used as a sensor and guide to determine correct positioning for administration of a spinal anesthesia.

In yet another preferred embodiment of the present invention, said device can be used as a sensor and guide to determine correct positioning for administration of chemotherapy specifically to a tumor.

As is known, in operations wherein tumorous tissue is excised, such as when a length of intestine is removed, the device of the present invention, in one of its preferred embodiments can be used in what is termed herein, tissue interrogation in that the margins of the excised tissue are examined using the device to determine whether said margins exhibit the characteristic density of normal or tumerous tissue.

In yet another preferred embodiment of the present invention, said device can be used as a sensor and guide to determine correct positioning for carrying out a spinal tap.

The invention also provides in its preferred embodiments a unitary device for analysis and extraction of tissue cells from a living body for biopsy testing, said device comprising a hollow biopsy needle having a sharpened distal end and a stylet disposed in said needle, said stylet comprising a cladded optical fiber sensor enveloped in a tubular jacket, wherein an uncladded area of said fiber and having a jacket window corresponding to said unclad area are proximate to said distal end, said optical fiber being linked at a proximate end to receive light from a light source, the device further including a light analyzer for measuring changes in qualities of output light as a result of the nature of the tissue being sensed at the depth at which said unclad area is positioned in said body during use, an electronic data processor being linked between said light analyzer and a display provided to show real-time data regarding any area evidencing a change in optical properties of body tissues being successively examined, said stylet being withdrawable from said hollow needle to allow injection of liquid material into said needle and/or for the collection of tissue cells from said area.

In a preferred embodiment of the present invention there is provided a device for the analysis of tissue cells, wherein said optical fiber is linked to a light-transmitting source, to an optical coupler and to a light analyzer for measuring, via an opening provided in said cladding, optical qualities of tissues at the depth at which said unclad area of said optical fiber is positioned, to determine an area evidencing change in optical density as a function of reflection, refraction and combinations thereof of the light within said fiber.

In a most preferred embodiment of the present invention there is provided a device wherein said quality of the output light reflects the nature of the tissue being sensed, comprises the refractive index at the interface between said unclad area of said optical fiber and body tissue in contact therewith.

In further preferred embodiments there is described a device wherein said light analyzer measures the ratio of light power transmitted/light power output received to determine an evanescent wave exiting the side of said optical fiber and its degree of absorption by adjacent body tissue.

In further embodiments said incoming light source is a laser beam or a light emitting diode.

In yet other embodiments said output light is amplified and converted to a voltage by a photodiode, data regarding said voltage being shown on said display.

Also, said light analyzer can be an interferometer, a polarimeter, or spectrometer.

In another aspect of the present invention there is disclosed a device wherein said light source is adapted to generate light of multiple wavelengths and said light analyzer is a spectrophotometer.

The jacket of the probe can be metallic or made of a plastic. Described embodiments include a jacket and said cladding removed proximate to said distal end in a cylindrical or in a side surface configuration. The distal end of the optical fiber is arranged to provide substantially total reflectance, and in contradistinction to prior art devices is not used to receive light from illuminated tissue.

In another aspect of the present invention there is provided a method for real time analysis and identification of surrounding tissue using a biopsy instrument having a needle-like distal end with a stylet incorporated therein, said stylet being based on an optical fiber as its core, wherein said optical fiber is linked to a light source and a light analyzer, said method comprising the steps of:
(a) inserting said needle into tissue to be examined;
(b) transmitting a light signal via said optical fiber within said needle; and
(c) measuring optical qualities of tissue at the area reached by an unclad portion of said fiber to determine an area evidencing change in optical density.

In preferred embodiments of the present invention said method is used to determine the location of guide wires and other devices within a body.

In other preferred embodiments said method is used to determine clean margins following an excision of unhealthy tissue.

In yet other preferred embodiments said method is used to determine characteristics of abnormalities of body tissues.

In especially preferred embodiments wherein said method is used to determine characteristics of abnormalities of body tissues, said abnormalities are plaques within blood vessels, however said method can also be used to determine any other abnormalities that may be found.

The invention also provides a method of real time tissue diagnosis and extraction of tissue or other material from a body using a biopsy instrument having a needle-like distal end with a stylet incorporated therein, said stylet having an optical fiber incorporated therein, wherein said optical fiber is linked to a light source and a light analyzer, said method comprising the steps of:
(a) inserting said needle into tissue to be examined;
(b) transmitting a light signal via said optical fiber within said needle;
(c) measuring optical qualities of tissue at the area reached by an unclad portion of said fiber to determine an area evidencing change in optical density;
(d) withdrawing the stylet and causing liquid to be ejected from the distal end of said instrument in said area of changed optical density;
(e) causing reverse pressure to form at the distal end of such instrument so that said liquid and biopsy cells from said area of changed optical density are retrieved into said instrument; and
(f) extracting said cells from said tissue, In a further embodiment of the invention, said light analyzer is connected through an optical coupler to the optical fiber within said stylet.

It will thus be realized that the novel device of the present invention serves to analyze the interaction of light with tissue. The system utilizes a thin optical fiber probe (stylet) that can be independently used or passed down a needle and into contact with the tissue to be examined. Light is delivered to the place of contact with the tissue via the optical fiber stylet. At the same time the distal part of the stylet, placed in the needle, functions as the fiber optic probe.

The basis of the invention is that cancerous or other abnormal tissue reflects, refracts, scatters and absorbs light differently than does healthy tissue. For example, cancerous tissue can contain different chromphores (or different concentrations of certain chromophores) as compared to adjacent healthy tissue. Further, cell morphology is also different in cancerous or other abnormal tissue, and a malignant tumor sharply changes the tissue density. Therefore the process of light's reflection/refraction on the stylet (optical fiber)-tissue boundary (in the place where the bared fiber contacts a tissue) for cancerous tissue are different from those of normal tissue. This difference results in differences in optical parameters such as wave amplitude, phase, and polarization of the output light.

The sensor configuration employed in the invention relies on the interaction of the evanescent light wave (at the uncoated part of the fiber) and the target tissue". The evanescent wave is the exponentially decaying electromagnetic field that penetrates a short distance into the low index medium (the tissue or substance being examined), when the total internal reflection occurs at a silica core/tissue interface. The degree of penetration, and correspondingly the properties of the light which has remained inside the optical fiber is a function of optical properties of the optic fiber core and the ambient tissue in contact therewith.

The stylet can be manufactured in a metal jacket multimode silica/silicone or other plastic optical fiber.

The transmitted light (after reflection from the remote end of the fiber) in the input end of the fiber can be sensed by a light analyzer, typically based on a silicon photodiode. The transmitted light is converted to a voltage through an electronic module, which contains an amplifier, a processor and a comparator. The voltage signals are amplified and compared with an array of previously determined signals characteristic of potentially healthy tissue. The processor may also include a digital recording system and computer memory, permitting the signals received by the light analyzer from different tissue depths to be stored for later revue and analysis by a supervising clinician.

Another option is a real time display screen, with signals supplied by a microprocessor, as well as a visual or audible alarm signal for real time warning when the needle reaches a depth where the tissue characteristics are abnormal and from where the clinician should take an additional sample.

The disclosed technology lets the physician perform the biopsy in the same manner to which he/she is accustomed. As in the needles used today, the stylet remains in the needle until a cell sample is to be collected and contacts the surrounding tissue only in a very small area. The device of the present invention enables the stylet to act as a sensor and identify the nature of the tissue surrounding the needle. The exposure of the sensing stylet is facilitated through a simple movement of the stylet or needle in a way that a surface proximate to the tip of the stylet, where the sensing point is located, meets the surrounding tissue. The stylet may also be exposed through a small 'window' on the side of the needle.

The technique and method of the present invention enables the physician to determine the tissue the needle tip is located in and thereby enabling him/her to know that he/she is taking the sample from the correct location. The technique makes use of the stylet located in the needle, which normally functions as a mechanical tool. In the present invention, the stylet is used as an optical sensor, providing real-time results, which may be used for further guidance of the biopsy needle.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3 and 4 are diagrams showing a clad fiber and indicating light leakage into the cladding.

FIG. 5 is a block diagram of an arrangement for converting output light into an observable and measurable format;

FIG. 6 is a detail perspective view of a stylet and needle end;

Figure 1:
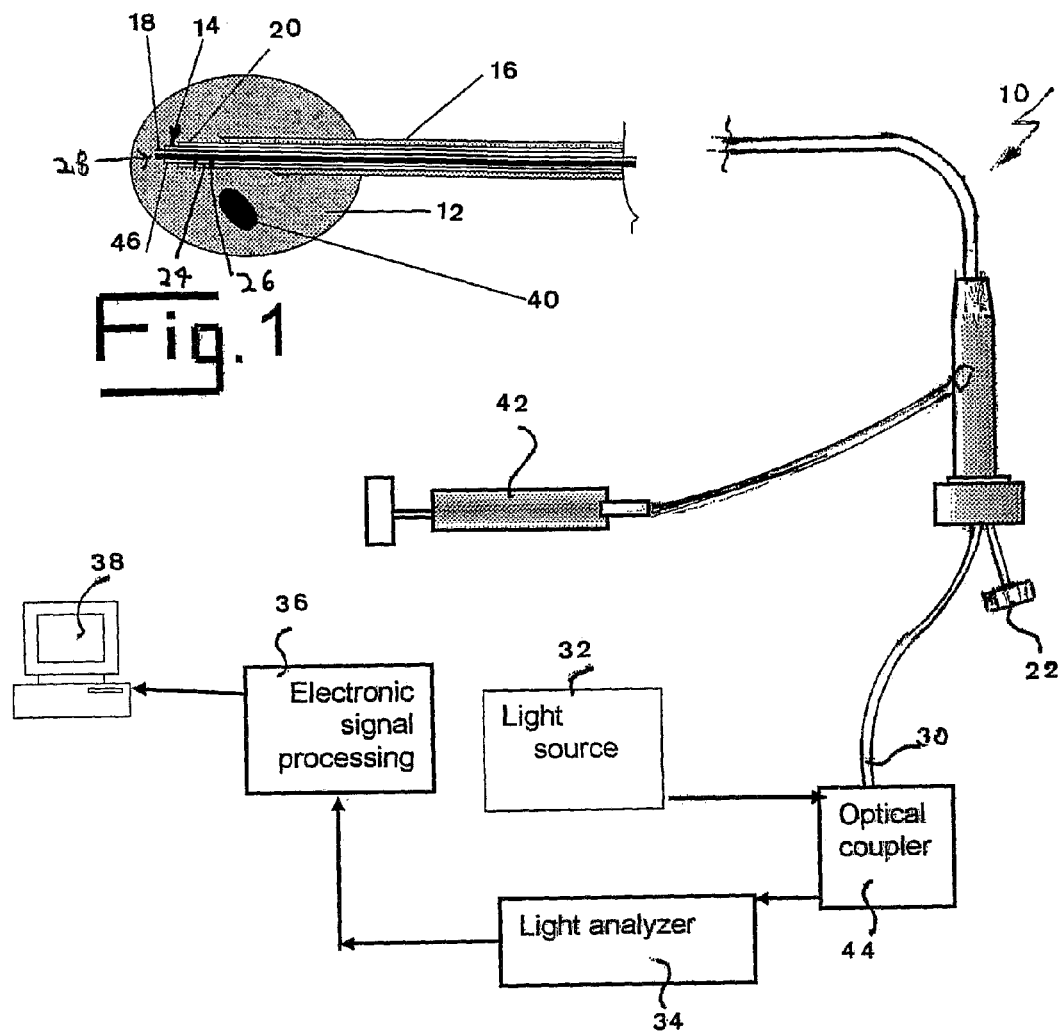
FIG. 1 is a diagrammatic view of a preferred embodiment of the device according to the invention.

There is seen in FIG. 1 a unitary device 10 for sensing and analysis and extraction of tissue cells from a living body tissue 12 for biopsy testing.

Seen is a device comprising a hollow needle 16 having a sharpened distal end. A stylet 14, which is used to steer the needle 16 is disposed in the needle hollow center. The stylet 14 comprises an optical fiber sensor 18 provided with cladding 46 enveloped in a tubular jacket 20, and is advanced into the body tissue 12 by actuating the pusher 22 seen in the diagram.

A suitable example of an optical fiber 18 for the present purpose is a metallized PCS 300, core diameter 150 μm, the refractive indices of the core and the cladding being 1.457 and 1.407, respectively.

The tubular jacket 20 is metallic, suitably made of stainless steel.

As will be seen in detailed views in FIGS. 2, 6, 7 and 10, the optic fiber 18 has a small unclad area 24, which is exposed to body tissue 12 when in use due to a jacket window 26 slightly larger than the unclad area 24, which is disposed proximate to the distal end 28 of the optic fiber 18. It is to be recognized however, that this is only one of many possible arrangements.

The optical fiber 18 is linked at a proximate end 30 to receive light from a light source 32. An optical coupler is used for both sending to, and receiving light from stylet 14.

The type of light provided corresponds to the optical property to be used for analysis. Accordingly, incoming light source 32 may be a laser, or a light emitting diode with a collimated visible beam (e.g. 670 nm), or an infrared beam (e.g. 840 nm), which is injected into the optical fiber 18.

A light analyzer 34 at the proximate end of the stylet measures selected qualities of output light. Thus, the light analyzer 34 may be an interferometer, a polarimeter. or spectrometer.

An electronic data processor 36, which may be integral with a computer is linked between the light analyzer 34 and a display 38 provided to show real-time data regarding any area 40 evidencing a change in optical properties of body tissues 12 being successively examined. The object of the procedure is to determine an area 40 evidencing change in optical density as a function of reflection, refraction and/or combinations thereof of the light within the fiber 18.

The stylet 14 is withdrawable from the hollow biopsy needle 16 to allow injection of liquid by means of a syringe 42 into the needle 16 and for the collection of suspected tissue cells from the area 40.

With regard to the rest of the figures, similar reference numerals have been used to identify similar parts.

Figure 2:
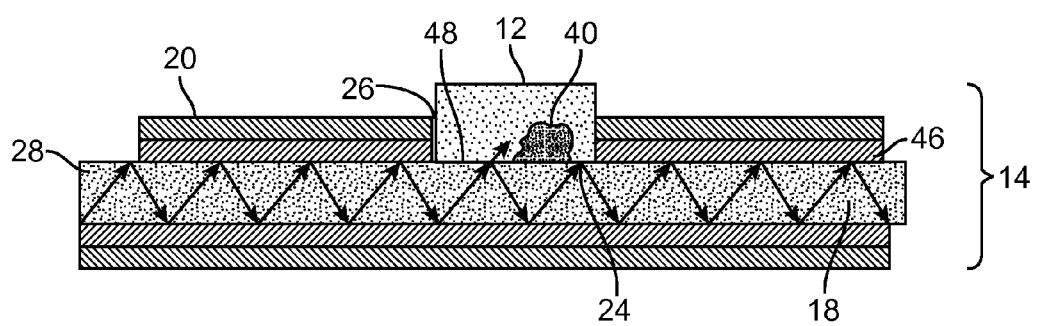
FIG. 2 is a sectional elevation of the device wherein the light in the fiber is refracted at the cladding inner walls.

Referring now to FIG. 2, there is seen a detail of a stylet 14 wherein the property of the output light from the target tissue 12 comprises the refractive index at the interface 48 between the unclad area 24 of the optical fiber 18 and body tissue 12 in contact therewith. The change in the refractive index, exaggerated for illustrative purposes, which is detected as the stylet 14 moves from healthy tissue 12 to a malignant area 40 is signaled by the stylet 14 and transferred in real time to the display screen 38 seen in FIG. 1.

FIGS. 3 and 4 illustrate a detail of a unitary device 50, wherein a light analyzer 34, seen in FIG. 1, measures the ratio of light power transmitted/light power output received.

This ratio is used to calculate the light power of an evanescent wave 52 exiting the side of the optic fiber 54 and its degree of absorption by adjacent body tissue 12 seen in FIG. 1.

As seen in FIG. 4, the graph 58 shows the light intensity inside and outside the optic fiber core 56 seen in FIG. 3. The evanescent field is formed by light escaping the boundaries of the core 56. Light intensity—depicted in the graph 58 is much higher in the center of the optic fiber than at its outer face 54. As is seen, a portion of the light penetrates into the cladding 62, thus where the cladding is removed as seen in FIG. 2 such light will instead enter body tissue 12 seen in FIG. 1.

Referring now to FIG. 5, there is represented a detail of a unitary device 64 wherein the output light is amplified at 66 and converted to a voltage 68 by a photodiode 70, data regarding the voltage 68 being shown on the display 72.

FIG. 6 shows a detail of a unitary device wherein the stylet jacket 74 is made of a plastic. The portion of the jacket 74 and the cladding 76 removed is proximate to the distal end 78 of the fiber optic 80. Thus a window 82 is formed which has a side surface configuration.

Figure 7:
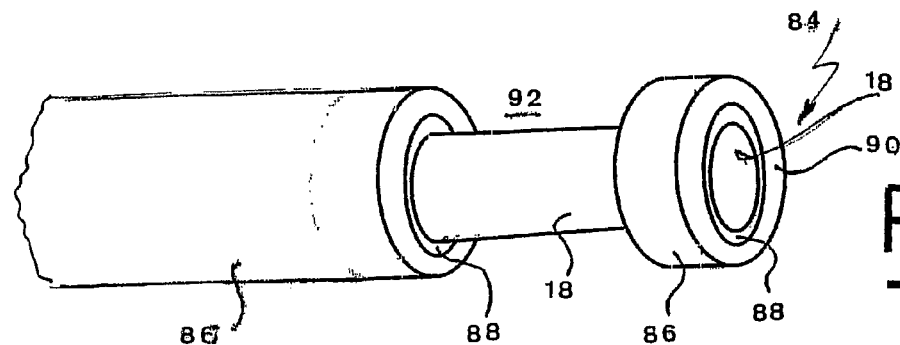
FIG. 7 is a perspective detail view of a further embodiment of the stylet window.

FIG. 7 illustrates a detail of a stylet 84 wherein the portion of the jacket 86 and the cladding 88 is removed is proximate to the distal end 90. The window 92 formed has a cylindrical configuration.

Figure 8:
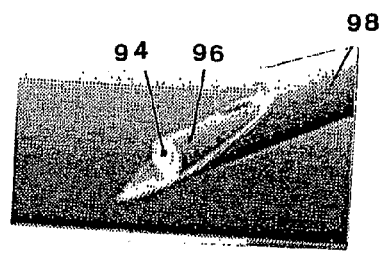
FIGS. 8, 9 and 10 are photographic views of the distal end of the stylet.

Seen in FIG. 8 is a photographic image of a further embodiment of the distal end of the optical fiber, which is arranged to provide substantially total reflectance. The fiber extremity is cut precisely perpendicularly to its axis and the resultant circle 94 is given a metal coating. The stylet 96 is seen disposed in the biopsy needle 98.

Figure 9:
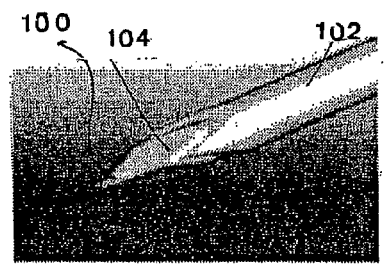

Referring now to FIG. 9, there is depicted an embodiment wherein the distal end of the stylet 100, as well as of the needle 102, has a triangular configuration 104, which reduces the force needed to advance the probe into the body tissue, and yet is arranged to provide substantially total reflectance in the optic fiber.

Figure 10:
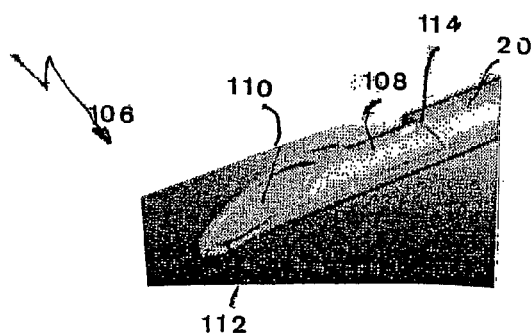

FIG. 10 shows a stylet 106 wherein the distal extremity of the fiber optic 108 is sharply angled and metal coated on its sloping face 110. The stylet 106 has a silicon core and polymer coating cladding 112. A side window 114 is formed by removal of a section of the cladding 112.

The present invention also includes the following method of use for the unitary device 10 seen in FIG. 1:

A method of real time tissue diagnosis and extraction of biopsy cells from a body using a biopsy instrument having a needle-like distal end with a stylet incorporated therein, the stylet being based on an optical fiber as its core, wherein the optical fiber is linked to a light source and a light analyzer, the method comprising the steps of:
(a) inserting the needle into tissue to be examined;
(b) transmitting a light signal via the optical fiber within the needle;
(c) measuring optical qualities of tissue at the area reached by an unclad portion of the fiber to determine an area evidencing change in optical density;
(d) withdrawing the stylet and causing liquid to be ejected from the distal end of the instrument in the area of changed optical density;
(e) causing reverse pressure to form at the distal end of such instrument so that the liquid and biopsy cells from the area of changed optical density are retrieved into the instrument; and
(f) extracting the cells from the tissue, Preferably, the light analyzer is connected through an optical coupler to the optical fiber within the stylet.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for analysis of tissue cell characteristics in a living body, said device comprising:
   (a) a light source;
   (b) a stylet comprising an integral core of an optical fiber sensor enveloped in a tubular metallic jacket,
   wherein an unclad area of said sensor and a jacket window adjacent to said unclad area are proximate to the distal end of the stylet, thereby constituting a laterally facing optical sensing area along an outer surface of said stylet,
   wherein said stylet is configured at a proximate end to receive light from the light source and to transmit the light from the distal end into tissue at or around the sensing area,
   (c) a light analyzer configured to measure one or more qualities of light received from tissue at or around the laterally facing optical sensing area;
   (d) a data processor configured to receive signals about the qualities of the light from the light analyzer, to compare said signals with signals characteristic of healthy tissue, and thereby to determine whether tissue at or around the sensing area has optical properties characteristic of cancerous cells;
   (e) a display configured to receive information from the data processor and to display in real time whether tissue being analyzed by the device has optical properties characteristic of cancerous cells.

2. A device according to claim 1, wherein a change in optical density of tissue characteristic of cancerous cells is determined as a function of reflection, refraction, absorption or a combination thereof of light transmitted and received at the distal end of the stylet.

3. A device according to claim 1, wherein a quality of light measured by the light analyzer comprises the refractive index at the interface between said sensing area of the stylet and normal or cancerous body tissue in contact therewith.

4. A device according to claim 1, wherein said light analyzer measures the ratio of light power transmitted/light power output received to determine the light power of an evanescent wave exiting the side of said sensing area and its degree of absorption by adjacent body tissue.

5. A device according to claim 1, wherein said light source is a laser beam.

6. A device according to claim 1, wherein said light source is a light emitting diode.

7. A device according to claim 1, wherein light received from tissue at or around the sensor area is amplified and converted to a voltage by a photodiode, data regarding said voltage being shown on said display.

8. A device according to claim 1, wherein said light analyzer is an interferometer.

9. A device according to claim 1 wherein said light analyzer is a polarimeter.

10. A device according to claim 1 wherein said light source is adapted to generate light of multiple wavelengths and said light analyzer is a spectrophotometer.

11. A device according to claim 1 wherein said jacket window and said unclad area proximate to said distal end have a cylindrical configuration.

12. A device according to claim 1 wherein the distal end of the stylet is arranged to provide substantially total reflectance.

13. A method for real time analysis and identification of surrounding tissue using a device according to claim 1, said method comprising the steps of
(a) inserting said stylet into tissue to be examined;
(b) transmitting a light signal via said stylet into the tissue; and
(c) measuring optical qualities
of light received from the tissue to determine if tissue at or around the sensing area of the stylet has optical parameters characteristic of cancerous tissue.

14. A method according to claim 13 wherein said method is also used to determine the location of guide wires and other devices within a body.

15. A method according to claim 13 wherein said method is used to determine clean margins following an excision of unhealthy tissue.

16. A method of real time tissue diagnosis and extraction of biopsy cells from a body using
a device according to claim 1, said method comprising the steps of:
(a) inserting said stylet into tissue to be examined;
(b) transmitting a light signal via said stylet into the tissue;
(c) measuring optical qualities
of light received from the tissue to determine if tissue at or around the sensing area of the stylet has optical parameters characteristic of cancerous tissue;
(d) withdrawing the optical fiber from the stylet and causing liquid to be ejected from the distal end of the stylet into an area of changed optical density;
(e) causing reverse pressure to form at the distal end so that said liquid and biopsy cells from said area of changed optical density are retrieved into the device; and
(f) extracting said biopsy cells from said tissue.

17. A device according to claim 1, wherein said light analyzer is connected through an optical coupler to the stylet.

18. A device according to claim 1 wherein the data processor is configured to receive signals from the light analyzer wirelessly.

19. A device according to claim 1 wherein said jacket window and said unclad area proximate to said distal end have a side surface configuration.

20. A device according to claim 1, wherein the tubular metallic jacket enveloping said stylet is a hollow biopsy needle with a sharp distal tip,
wherein the stylet is configured such that it may be used to guide placement of the biopsy needle, and thereafter withdrawn from the biopsy needle such that a substance may be injected through the biopsy needle and/or a tissue sample may be collected thereby.

21. A device according to claim 20, further comprising a visual or audible alarm that is configured to indicate to a clinician operating the device when the needle has reached an area where characteristics of tissue at or around the sensing area are sufficiently abnormal to take a biopsy sample.

* * * * *